United States Patent
Dees, Jr. et al.

(10) Patent No.: US 10,779,894 B2
(45) Date of Patent: Sep. 22, 2020

(54) SURGICAL NAVIGATION SYSTEM SUPPORT ARRAY

(71) Applicant: Smith & Nephew, Inc., Memphis, TN (US)

(72) Inventors: Roger Ryan Dees, Jr., Drummonds, TN (US); Branislav Jaramaz, Pittsburgh, PA (US); Scott Kennedy Laster, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/489,107

(22) PCT Filed: Feb. 27, 2018

(86) PCT No.: PCT/US2018/020036
§ 371 (c)(1),
(2) Date: Aug. 27, 2019

(87) PCT Pub. No.: WO2018/157161
PCT Pub. Date: Aug. 30, 2018

(65) Prior Publication Data
US 2020/0060769 A1    Feb. 27, 2020

Related U.S. Application Data

(60) Provisional application No. 62/463,853, filed on Feb. 27, 2017.

(51) Int. Cl.
*A61B 34/20* (2016.01)
*A61B 90/00* (2016.01)
(Continued)

(52) U.S. Cl.
CPC .......... *A61B 34/20* (2016.02); *A61B 17/1725* (2013.01); *A61B 17/72* (2013.01);
(Continued)

(58) Field of Classification Search
CPC ...................................................... A61B 34/20
See application file for complete search history.

(56) References Cited

U.S. PATENT DOCUMENTS

2005/0107790 A1 *  5/2005  Qian ................... A61B 17/7266
                                                          606/62
2006/0084867 A1    4/2006  Tremblay et al.
(Continued)

FOREIGN PATENT DOCUMENTS

WO         9500085 A1    1/1995
WO      2014005225 A1    1/2014

OTHER PUBLICATIONS

International Search Report and Written Opinion for PCT/US2018/020036 dated May 25, 2018.

*Primary Examiner* — Rochelle D Turchen
(74) *Attorney, Agent, or Firm* — Troutman Pepper Hamilton Sanders LLP (57) ABSTRACT

A system (100) and device (300) for mounting and tracking a tracker array during a surgical procedure are described. For example, the system includes a surgical navigation system (700) including a position tracking system (702) configured to track one or more tracker arrays, and a device (300) for mounting a tracker array (306) onto a patient during the surgical procedure. The device includes an intramedullary (IM) canal component (304) configured to be inserted into an IM canal (310) within a bone (312). The device further includes a tracker pin (308) configured to penetrate at least a portion of the bone and engage an inserted end (411, 413) of the IM canal component, and a tracker array (306) affixed to the tracker pin. The IM canal component is configured to engage the IM canal of the bone to stabilize the tracker array during the surgical procedure.

20 Claims, 7 Drawing Sheets

(51) Int. Cl.
*A61B 17/17* (2006.01)
*A61B 17/72* (2006.01)

(52) U.S. Cl.
CPC ...... *A61B 90/39* (2016.02); *A61B 2034/2048* (2016.02); *A61B 2034/2051* (2016.02); *A61B 2034/2055* (2016.02); *A61B 2090/3916* (2016.02); *A61B 2090/3983* (2016.02)

(56) References Cited

U.S. PATENT DOCUMENTS

| | | | |
|---|---|---|---|
| 2006/0098851 A1* | 5/2006 | Shoham | A61B 17/1703 382/128 |
| 2008/0021474 A1* | 1/2008 | Bonutti | A61B 17/0401 606/64 |
| 2013/0281884 A1 | 10/2013 | Mullaney et al. | |
| 2014/0276000 A1 | 9/2014 | Mullaney et al. | |
| 2015/0112344 A1 | 4/2015 | Shoham et al. | |
| 2016/0166408 A1 | 6/2016 | Murphy | |

* cited by examiner

SURGICAL NAVIGATION SYSTEM SUPPORT ARRAY

CLAIM OF PRIORITY

This application is a U.S. national stage filing under 35 U.S.C. § 371 of International PCT Application No. PCT/US2018/020036, filed Feb. 27, 2018, which claims the benefit of priority to U.S. Provisional Application No. 62/463,853, titled "Surgical Navigation System Support Array," filed Feb. 27, 2017, each of which is incorporated herein by reference in its entirety.

TECHNICAL FIELD

The present disclosure relates generally to a mounting device for use with a surgical navigation system. More specifically, the present disclosure relates to a mount for a fiducial array that can be used to provide a reference point for an intramedullary canal in bone to assist a surgeon in revision implant surgery.

BACKGROUND

The use of computers, robotics, and imaging to aid orthopedic surgery is known in the art. There has been a great deal of study and development of computer-aided navigation and robotic systems used to guide surgical procedures. For example, computer assisted surgery ("CAS") has been applied to invasive surgical procedures, such as implant procedures. Typically, surgical procedures that implement CAS techniques utilize a surgical navigation system to track anatomy, implements, instrumentation, trial implants, implant components and virtual constructs or references. Such systems can render images and data related to them in connection with orthopedic, surgical and other operations. CAS allows for the association of anatomical structures, constructs, and points-in-space with a fiducial array.

One CAS system, the NAVIO® surgical system, can be used to assist in uni-compartmental and total knee replacement surgeries. NAVIO is a registered trademark of BLUE BELT TECHNOLOGIES, INC, of Pittsburgh, Pa. The NAVIO® surgical system can provide surgical navigation during the removal of tissue and during the placement of cutting guides by employing tracker arrays that are mounted to the operative bones with bicortical pins that pass through or unicortical pins that pass at least partially into the intramedullary (IM) canal. Certain implant surgeries, however, are performed on weakened or diseased bone which is not strong enough to keep a tracker array in a firmly fixed position.

Another surgical system is the ORTHOPILOT® navigation system. ORTHOPILOT is a registered trademark of Aesculap Implant Systems, LLC of Center Valley, Pa. The ORTHOPILOT® navigation system performs tracking during knee replacement revision procedures. Tracker arrays are attached to the bone via extramedullary clamps; however, these types of clamps are less secure than bicortical or unicortical pins and can shift or otherwise move during a surgical procedure.

What are needed are methods and systems for securely inserting an IM component into a compromised operative bone to provide a frame of reference for navigation and tissue removal purposes.

SUMMARY

There is provided a device for mounting a tracker array. The device includes an intramedullary (IM) canal component configured to be inserted into an IM canal within a bone, the IM canal component comprising an inserted end and an exposed end, a tracker pin configured to penetrate at least a portion of the bone and engage the inserted end of the IM canal component, and a tracker array removably affixed to the tracker pin. The IM canal component is configured to engage at least a portion of the IM canal of the bone to stabilize the tracker array during a surgical procedure.

In certain embodiments, the inserted end of the IM canal component includes a first prong and a second prong. In some examples, the first prong comprises at least one aperture configured to receive the tracker pin. In some further examples, the inserted end is configured to expand and press against an inner surface of the IM canal upon advancement of the tracker pin. In some examples, the first prong and the second prong form a slot there between, the slot configured to receive at least a portion of the tracker pin.

In certain embodiments, the tracker pin includes at least one of a unicortical pin and a bicortical pin.

In certain embodiments, the exposed end of the IM canal component is configured to connect to one or more surgical components. In some examples, the one or more surgical components include at least one of a replacement joint implant component, a cut guide, and a saw guide.

In certain embodiments, the IM canal component further comprises embedded instrumentation configured to provide at least one of position and orientation information. In some examples, the embedded instrumentation comprises at least one of an accelerometer, a gyroscope, a magnetometer, an inertial measurement unit, and a global positioning system device.

There is also provided a system for tracking a tracker array during a surgical procedure. The system includes a surgical navigation system comprising a position tracking system, and a device for mounting a tracker array onto a patient during the surgical procedure. The device includes an intramedullary (IM) canal component configured to be inserted into an IM canal within a bone, the IM canal component comprising an inserted end and an exposed end, a tracker pin configured to penetrate at least a portion of the bone and engage the inserted end of the IM canal component, and a tracker array removably affixed to the tracker pin. The IM canal component is configured to engage at least a portion of the IM canal of the bone to stabilize the tracker array during the surgical procedure, and the position tracking system is further configured to track the tracker array removably affixed to the tracker pin during the surgical procedure.

In certain embodiments, the inserted end of the IM canal component comprises a first prong and a second prong. In some examples, the first prong comprises at least one aperture configured to receive the tracker pin. In some further examples, the inserted end is configured to expand and press against an inner surface of the IM canal upon advancement of the tracker pin. In some examples, the first prong and the second prong form a slot there between, the slot configured to receive at least a portion of the tracker pin.

In certain embodiments, the tracker pin comprises at least one of a unicortical pin and a bicortical pin.

In certain embodiments, the exposed end of the IM canal component is configured to connect to one or more surgical components. In some examples, the one or more surgical components include at least one of a replacement joint implant component, a cut guide, and a saw guide.

In certain embodiments, the IM canal component further comprises embedded instrumentation configured to provide at least one of position and orientation information. In some examples, the embedded instrumentation comprises at least one of an accelerometer, a gyroscope, a magnetometer, an inertial measurement unit, and a global positioning system device.

The example embodiments described above can provide various advantages over prior techniques. For example, the techniques as taught herein can reduce the chance that a tracker array will shift during a surgical procedure as a result of being improperly secured to a patient's bone or attached to weakened or diseased bone that is not strong enough to stabilize the array. The techniques also provide for a universal platform for mounting revision implant components, drill guides, cutting guides, and other similar components.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

The present disclosure describes example systems and methods of mounting a tracker array on a weakened or compromised operative cortical bone to enable the use of a surgical navigation system. In the following description, for purposes of explanation, numerous specific details are set forth in order to provide a thorough understanding of example embodiments. It will be evident to one skilled in the art, however, that the embodiments as described herein can be practiced without these specific details.

For the purposes of this specification, the term "implant" is used to refer to a prosthetic device or structure manufactured to replace or enhance a biological structure, either permanently or on a trial basis. For example, in a knee replacement procedure, an implant can be placed on one or both of the tibia and femur. While the term "implant" is generally considered to denote a man-made structure (as contrasted with a transplant), for the purposes of this specification, an implant can include a biological tissue or material transplanted to replace or enhance a biological structure.

As used herein, the term "bicortical pin" refers to a surgical pin that is inserted through cortical bone, passes through the intramedullary canal, and re-enters cortical bone on the other side of the intramedullary canal. The term "unicortical pin" refers to a surgical pin that passes through cortical bone and enters the intramedullary canal, but does not re-enter cortical bone.

The disclosed mounting system is particularly adapted for surgical procedures that utilize surgical navigation systems, such as the NAVIO® surgical navigation system. Such procedures can include knee replacement revision surgery in which the surgeon accesses an intramedullary canal within a bone. For example, the surgeon accesses the intramedullary canal to allow revision components outfitted with a stem to be fit or cemented in the bone canal.

In such procedures, the surgical navigation system relies on trackers securely affixed to the tibia and to the femur to track location and motion of the bones involved in the joint throughout the procedure. The trackers used with a surgical navigation system can be active or passive. For example, active trackers can include light emitting or electromagnetic trackers. Passive trackers can include, for example, reflective trackers. The trackers can provide a frame of reference for navigation of the joint throughout the surgical procedure.

Current systems utilize bicortical or unicortical bone pins to secure an array of trackers to the bone, which can become unstable depending on the quality of the bone and can impede the placement of an implant stem in the canal.

Figure 1:
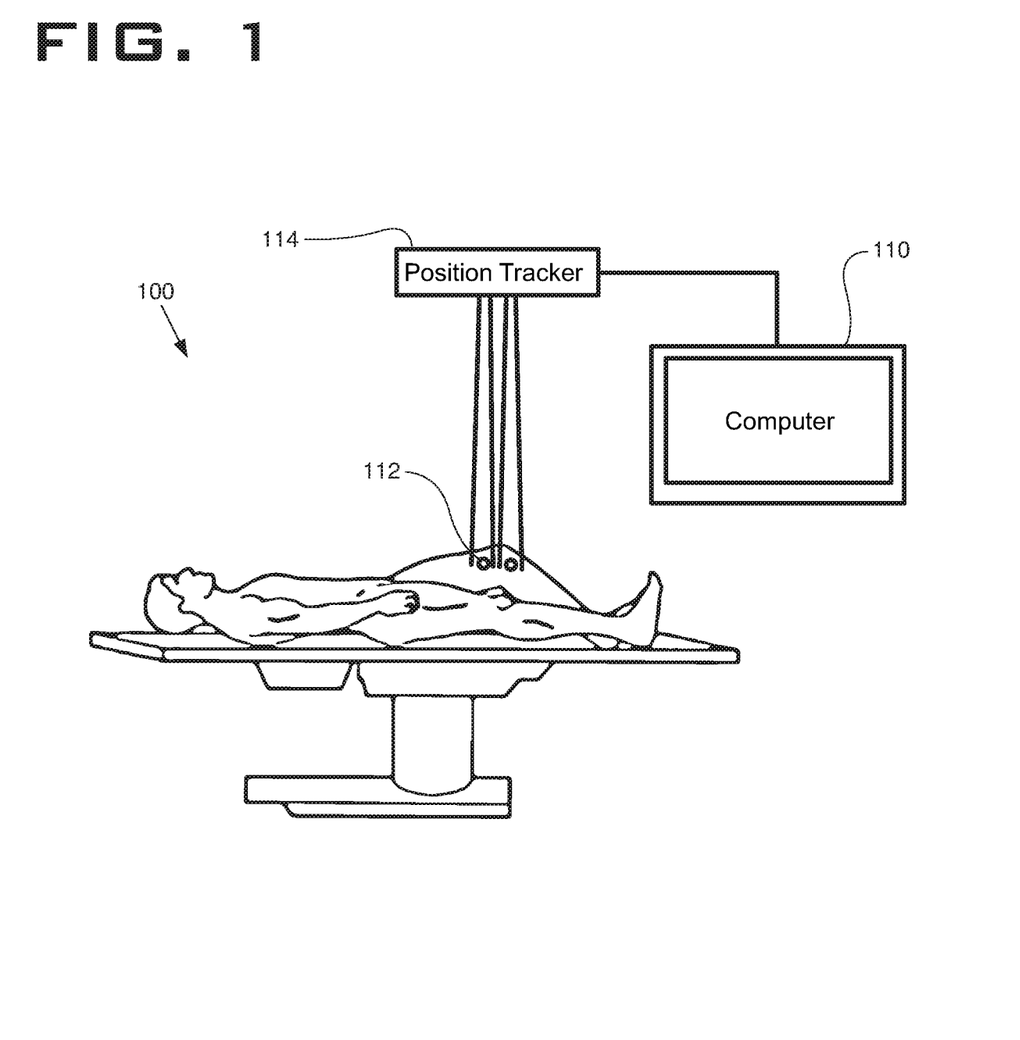
FIG. 1 depicts an illustration of an operating room with a system employing a surgical navigation system, in accordance with certain embodiments of the invention.

FIG. 1 illustrates various components of a surgical navigation system 100 that is configured to interface with a tracker array to determine locations of tracked objects in an operative space according to certain embodiments. The surgical navigation system 100 can assist a surgeon in performing certain surgical procedures, such as knee replacement revision surgery.

The surgical navigation system 100 includes a computer system 110 to provide a display for viewing location data provided by location trackers 112 as read by a position tracking system 114. In certain embodiments, the location trackers 112 are optical trackers and the position tracking system 114 employs an infrared camera system that can provide data relevant to the precise location of the bones in the knee joint. In certain embodiments, the position tracking system 114 can detect optical tracking spheres located on the location trackers 112 in order to gather location data regarding the femur and tibia for a patient upon whom a procedure is to be performed.

Figure 2:
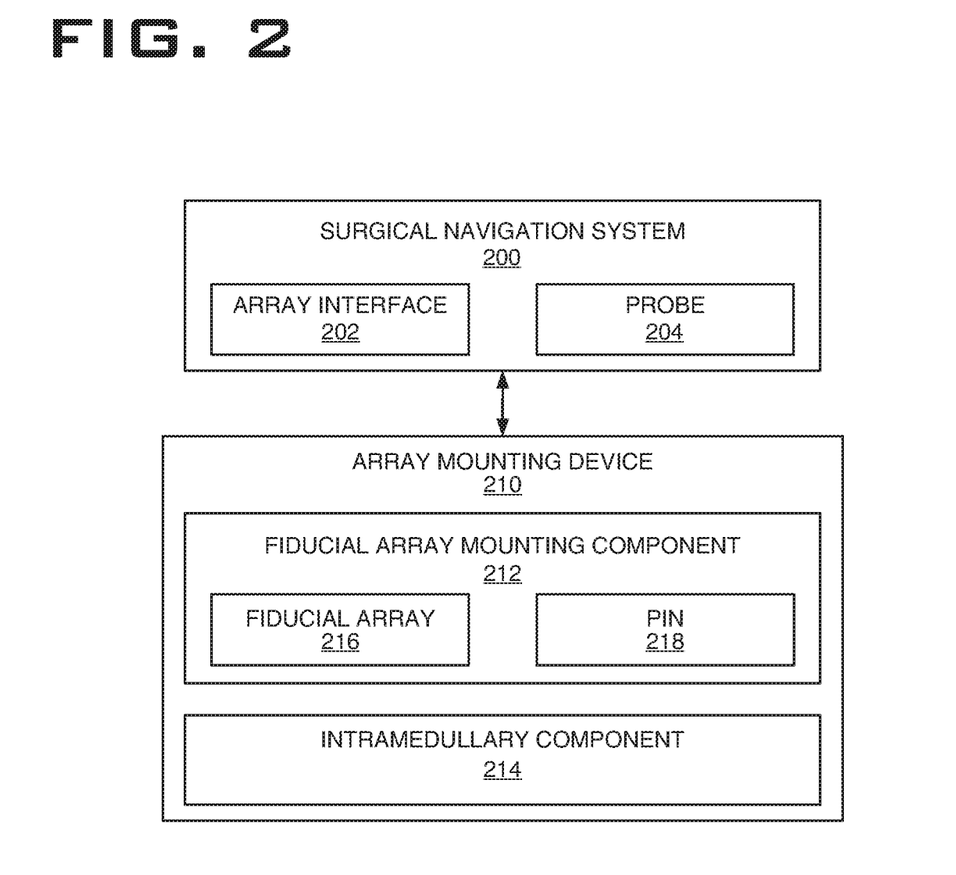
FIG. 2 depicts a block diagram depicting an array mounting device for mounting a tracker array to communicate with a surgical navigation system, in accordance with certain embodiments of the invention.

FIG. 2 illustrates a block diagram of the exemplary surgical navigation system, generally designated as 200, that includes at least an array interface 202 and a probe 204. The surgical navigation system 200 can configure the array interface 202 to detect the location of a mounting system or array mounting device 210. The probe 204 can be a surgical probe that is tracked by the surgical navigation system 200.

In certain embodiments, such as in a revision procedure in which a health care provider recommends removing and replacing a previously installed implant, the array mounting device 210 can include a mounting component 212 and an IM component 214. The IM component 214 can be configured to be placed within an IM canal. In certain implementations, the IM component 214 can be attached to a trial implant, cutting guide, or a drill guide, as will be discussed in further detail.

The mounting component 212 can include a fiducial array 216 (also called a tracker array herein) and a pin 218. The fiducial array 216 can be configured to fixably connect to the pin 218. In some examples, the pin 218 can be fixably engaged with the IM component 214 to provide the surgical navigation system 200 with precise location data for the component and any known implement attached thereto through the array interface 202.

The IM component 214, or other surgical implements that can be attached thereto, can be identified and registered to the surgical navigation system 200 by using the probe 204 and/or through point identification. The surgical navigation system 200 can identify the location of the probe 204 when directed by the surgeon to mark the location of identification points on an implant, trial, or tool.

In certain embodiments, the surgical navigation system 200 can be configured to use the probe 204 to examine a tapered cavity machined into a component, trial or other surgical tool for identification purposes. The probe 204 also can be utilized to identify a component, such as the intramedullary component 214, based upon parameters, such as one or more unique identification points and at least one vector formed by two or more of the identification points. These parameters can be matched to specific components, trial implants or surgical tools by varying the depth and the angle of the tapered hole in each such item.

Figure 3:
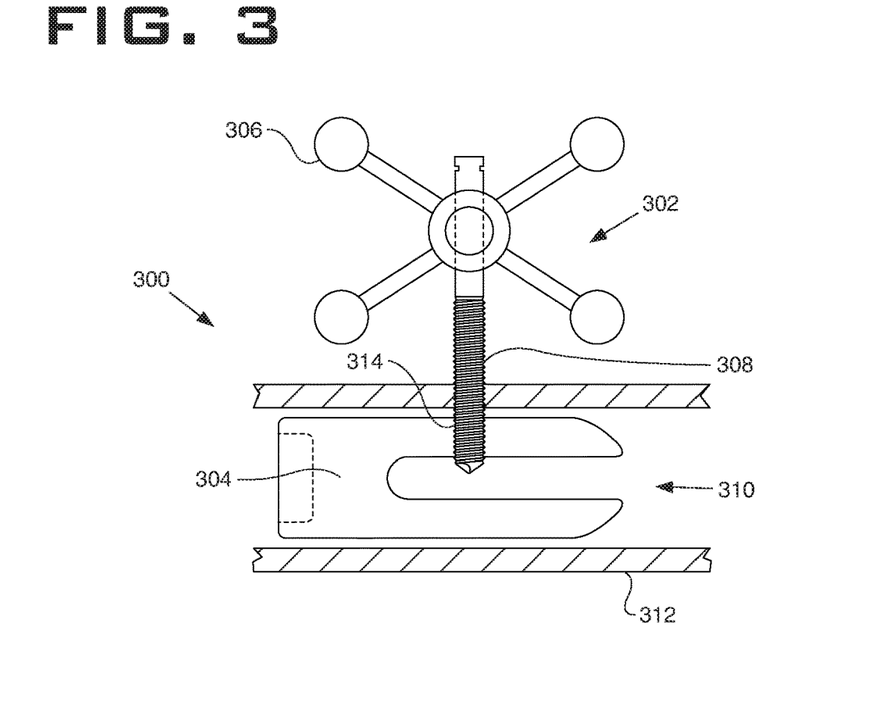
FIG. 3 depicts a sectional view in side elevation of an embodiment of the array mounting device described in FIG. 2, in accordance with certain embodiments of the invention.

FIG. 3 illustrates a cortical bone 312 with an IM canal 310 that has already had a previous implant removed. A mounting system or array mounting device, generally designated as 300, can include a fiducial array mounting component 302 and an IM component 304. In certain implementations, the fiducial array mounting component 302 can include an array 306 and a unicortical pin 308. Depending upon the design, the unicortical pin 308 can be threaded or unthreaded.

In certain implementations, the IM component 304 can be positioned in the IM canal 310 within bone 312. Those of skill in the art will recognize that IM component 304 can be manufactured in different sizes to accommodate different IM canal sizes. Alternatively, the size of the IM component 304 can be adjustable to accommodate various IM canal sizes.

In certain implementations, the unicortical pin 308 can be configured to interact with the IM component 304 during knee arthroplasty revision surgery. In certain embodiments, the unicortical pin 308 can be received by an aperture 314 in the IM component 304 to stabilize the fiducial array 306 in order to enable surgical navigation. The aperture 314 can be threaded or unthreaded to securely connect with the pin or screw. Those of skill in the art will recognize that other structures for connecting the pin 308 to the IM component 304 are possible.

Figure 4:
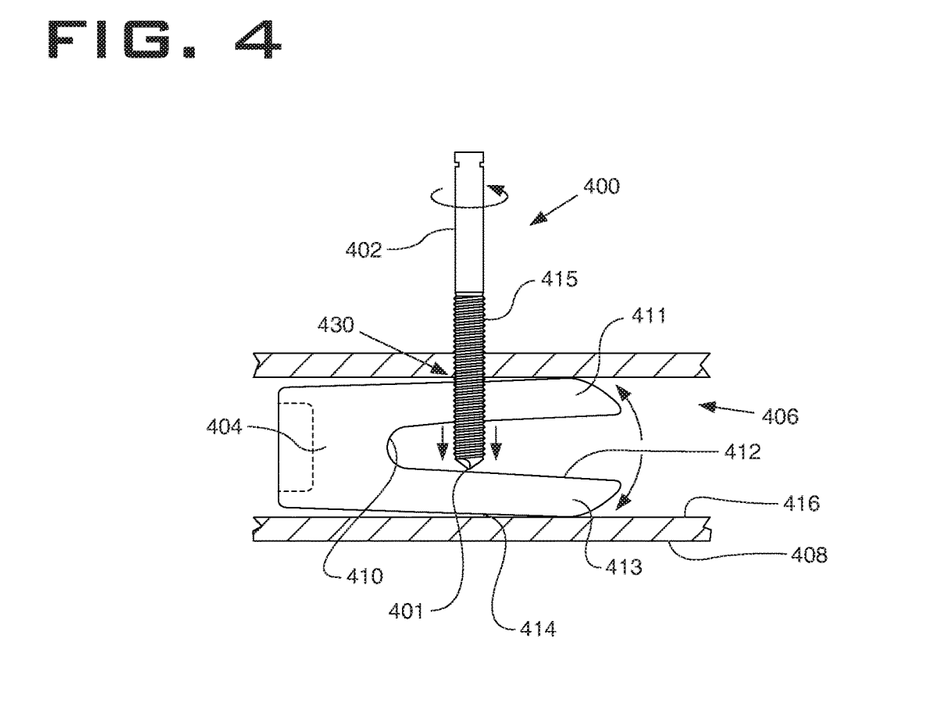
FIG. 4 depicts a sectional view in side elevation of an assembly of another embodiment of the array mounting device described in FIG. 2, in accordance with certain embodiments of the invention.

FIG. 4 illustrates an alternate assembly, generally designated as 400, of a mounting system or array mounting device. The assembly 400 can include a unicortical pin 402 and an IM component 404. As in FIG. 3, the IM component 404 can be positioned in an IM canal 406 within a bone 408 after, for example, a previously installed implant component has been removed. For example, the IM component 404 can be positioned within an IM canal in a patient's tibia after a previously installed tibial implant component has been removed.

In this exemplary embodiment, the IM component 404 can include a first prong 411 and a second prong 413 that are inserted into the IM canal. In some examples, the first prong 411 can form or otherwise include an aperture 430 sized to receive the unicortical pin 402. In the illustrated embodiment as shown in FIG. 4, the pin 402 includes threads 415 and the aperture is sized to matingly engage the pin 402.

As the unicortical pin 402 is screwed or otherwise inserted into and through the aperture 430, the unicortical pin is advanced through the intramedullary canal 406 and toward the second prong 413. After advancing through the intramedullary canal, a tip 401 of the unicortical pin 402 can engage or otherwise press against an inner surface 412 of the second prong 413. In some implementations, this engagement between the unicortical pin 402 and the inner surface 412 can cause the IM component 404 to expand. This expansion of the IM component 404 can cause an outer surface 414 of the second prong 413 to press against an inner surface 416 of the IM canal 406 to provide improved fixation of the component 404 in the IM canal 406. The resulting friction between the prongs 411, 413 and the inner surface 416 of the IM canal can provide for improved stability of the IM component during a surgical procedure.

In certain embodiments, additional ways of causing the prongs 411, 413 to press against the inner surface 416 of the IM canal 406 can be used. For example, a ratchet mechanism or a high friction connection between the pin 402 and the aperture 430 can be used to cause expansion of the prongs 411, 413. Connectors such as nails, or, alternatively, one or more compressible encasements around the pin 402 such as those used to securely attach a nail or screw to drywall can be used to improve the friction between the pin and the aperture 430, thereby causing force applied to the pin to cause expansion of the prongs 411, 413.

In other embodiments, both the first prong 411 and the second prong 413 can include apertures 430. In such an example, the pin 402 can be a threaded bicortical pin, and the thread rates are different for each aperture such that advancement of the pin forces the prongs 411, 413 against the inner surface 416 of the IM canal 406. In some embodiments, the bicortical pin 402 also may have more than one thread pitch.

Figure 5:
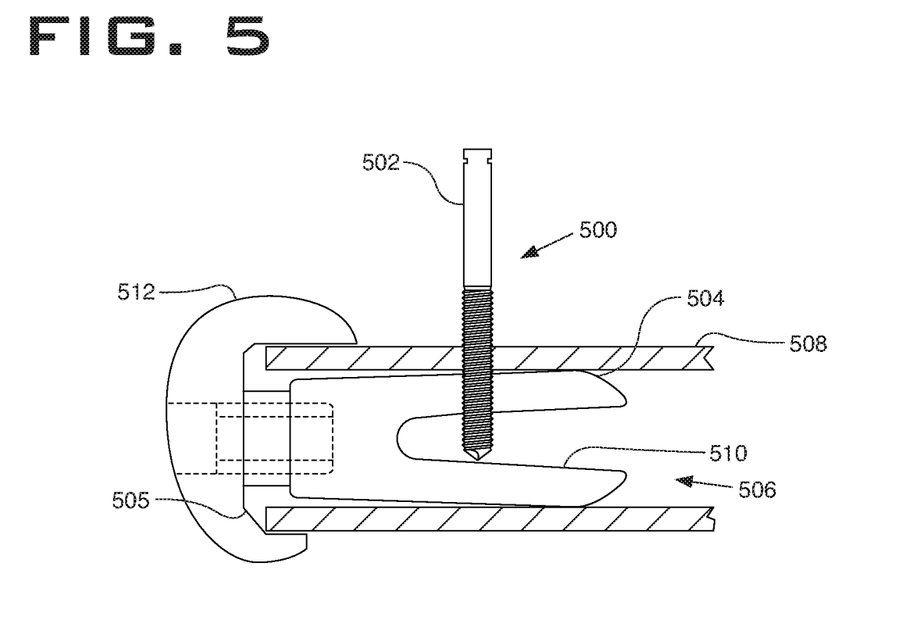
FIG. 5 depicts a sectional view in side elevation illustrating the placement of an assembly for another embodiment of the array mounting device described in FIG. 2, in accordance with certain embodiments of the invention.

FIG. 5 illustrates an alternate assembly 500 including a mounting system or array mounting device. The assembly 500 can include a unicortical pin 502 and an IM component 504. The IM component 504 can be securely positioned in an IM canal 506 within a bone 508 and has an exposed end 505 adapted to securely connect to surgical items such as adjustable cutting guides, drill guides, trial femoral components or trial tibia components. For example, as shown in FIG. 5, an implant component 512 can be securely connected to exposed end 505. As a result, the assembly 500 can provide a reference to a reconstructed joint line to a surgical navigation system, such as the surgical navigation system 100 shown in FIG. 1 or the surgical navigation system 200 shown in FIG. 2.

In certain implementations, where the quality of bone is sufficient for mounting a tracker array and the IM component 504 and the pin 502 are stable without connecting them as discussed in previous figures, the pin 502 does not pass through an aperture in the IM component 504. Rather, the pin 502 can be configured to pass through an open-ended slot 510 formed by the prongs of the IM component 504 to allow for unimpeded removal and reinsertion of the IM component 504, such as with multiple trial implants for sizing purposes, without the need to remove the pin 502. It should be noted that while a unicortical pin 502 is illustrated in FIG. 5, a bicortical pin also can be used in the situation where the pin 502 does not engage the IM component 504.

Figure 6:
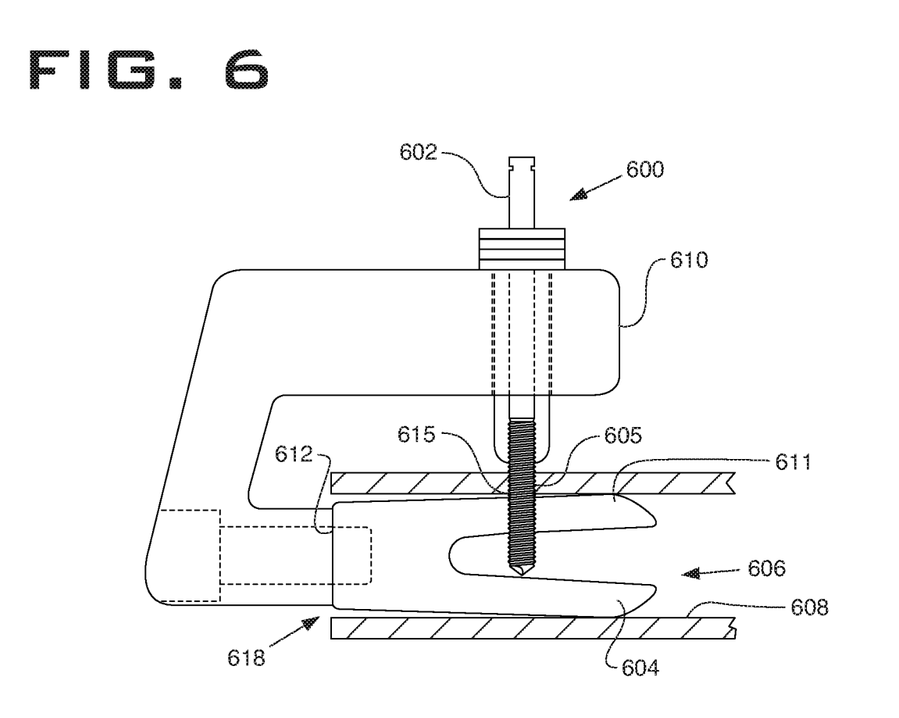
FIG. 6 depicts another sectional view in side elevation illustrating the placement of an assembly for another embodiment of the array mounting device described in FIG. 2, in accordance with certain embodiments of the invention.

FIG. 6 illustrates assembly 600 of another example of a mounting system or array mounting device as described herein. The assembly 600 can include a unicortical pin 602 and an IM component 604. In certain implementations, assembly 600 can be configured to provide for proper placement of the IM component 604. In many revision cases, bone is lost during removal of earlier implants, necessitating the use of augments. This bone loss makes it difficult to know whether the IM component 604 is placed properly in the IM canal 606 so that it acts as a reference to the desired joint line. In this embodiment as shown in FIG. 6, the IM component 604 can be positioned in the IM canal 606 and an imaging modality, such as fluoroscopy, can be used to verify correct positioning.

In some examples, a drill guide 610 can be attached to an exposed end 618 of the IM component 604. In certain implementations, the drill guide 610 is configured to be sufficiently sized such that it can be automatically positioned to drill a hole in the bone 608 at the exact position where an aperture 615 is located on a first prong 611 of the IM component as is illustrated in earlier figures. The drill guide 610 provides the correct placement and trajectory for implantation of the unicortical pin 602. In certain implementations, the drill guide 610 can be slideably adjusted to accommodate for intramedullary components 604 of varying sizes.

Figure 7:
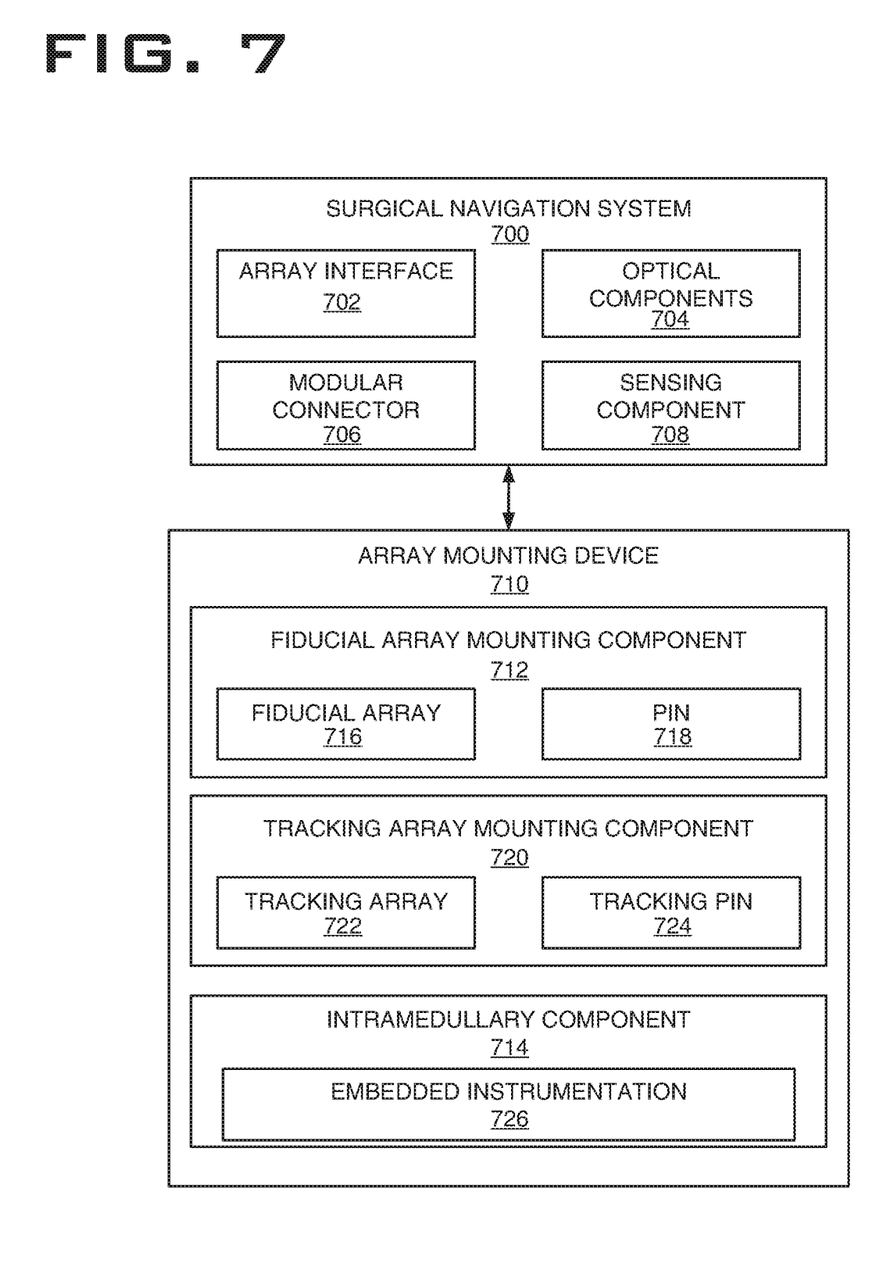
FIG. 7 depicts a block diagram depicting another embodiment of an array mounting device for mounting a tracker array to communicate with a surgical navigation system, in accordance with certain embodiments of the invention.
Figure 8:
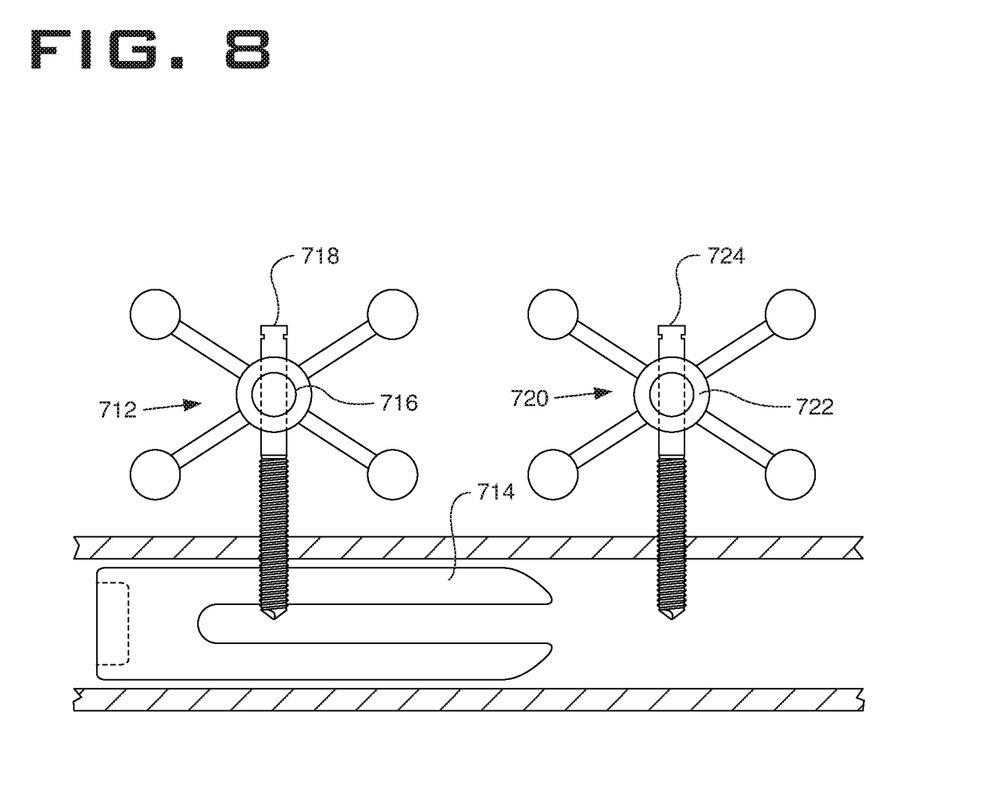
FIG. 8 depicts a sectional view in side elevation of the embodiment of the array mounting device described in FIG. 7, in accordance with certain embodiments of the invention.
Figure 9:
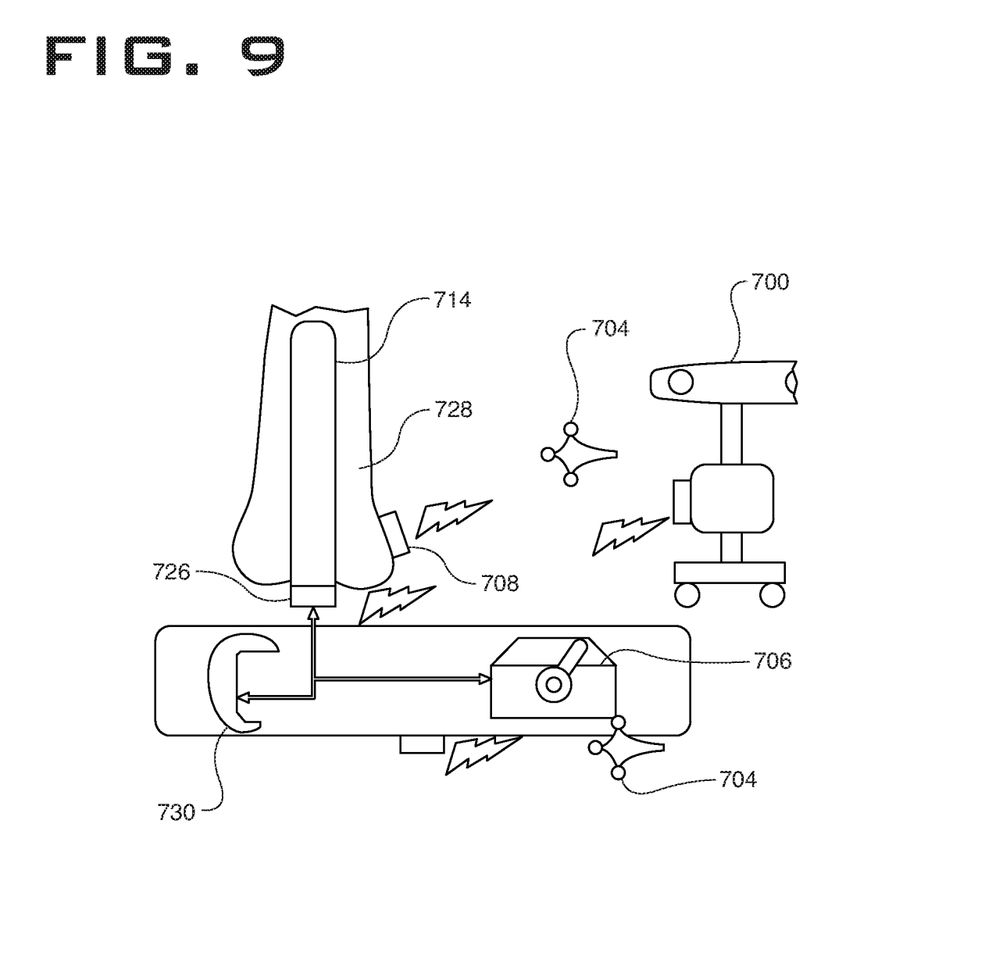
FIG. 9 depicts a side view of instruments that interface with the array mounting device described in FIG. 7, in accordance with certain embodiments of the invention.

FIGS. 7-9 illustrate a surgical navigation system 700. In certain implementations, the system 700 can include an array interface 702, a plurality of optical components 704, a modular connector 706, and a sensing component 708. The array interface 702 can be configured to communicate with a mounting system or array mounting device 710. In some examples, the optical components 704 can be reflective trackers or active trackers. For example, the optical components 704 can include reflective spheres.

The array mounting device 710 can include a fiducial array mounting component 712 and an IM component 714. The fiducial array mounting component 712 can include a fiducial array 716 and a pin 718. Unlike the embodiments shown in FIGS. 1-6, the array mounting device 710 can also include a tracking array mounting component 720. The tracking array mounting component 720 includes a tracking array 722 and a tracking pin 724.

As shown in FIG. 8, the tracking array 722 can be placed further from a knee joint (distal tibia, proximal femur) to provide a position reference for the fiducial array 716. The tracking array 722 can be used to store the relative position of the implant components or first tracker array on a temporary basis in the event that the fiducial array mounting component 712 and/or the IM component 714 need to be removed for any reason.

Referring now to FIG. 9, in certain embodiments, the IM component 714 can include embedded instrumentation 726 that provides the ability to make position and/or orientation estimates for an implant (not shown). The embedded instrumentation 726 can include active sensing components, such as accelerometers, gyroscopes, magnetometers, inertial measurement units, and a global positioning system (GPS) device. These sensing components can be attached to the intramedullary component 714, sealed within the intramedullary component 714, and/or affixed to the surface of a bone 728. The embedded instrumentation 726 can communicate with or interface with the active sensing component 708. In further embodiments, electromagnetic tracking systems could be used with electromagnetic trackers embedded in the IM components 714.

In some examples, the surgical navigation system 700 can be configured to implement the modular connector 706 and the embedded instrumentation 726 to register implants 730 or surgical tools (not shown) automatically, through the use of a known library of geometries. In certain implementations, the surgical navigation system 700 can perform auto-registration operations using a single tapered cavitation in the implant 730.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A device for mounting a tracker array, the device comprising:
   an intramedullary (IM) canal component configured to be inserted into an IM canal within a bone, the IM canal component comprising:
      an inserted end having a first prong and a second prong forming a slot therebetween, and
      an exposed end;
   a tracker pin configured to penetrate at least a portion of the bone and engage the inserted end of the IM canal component, wherein the slot is configured to receive at least a portion of the tracker pin; and
   a tracker array removably affixed to the tracker pin,
   wherein the IM canal component is configured to engage at least a portion of the IM canal of the bone to stabilize the tracker array during a surgical procedure.

2. The device of claim 1, wherein the first prong comprises at least one aperture configured to receive the tracker pin.

3. The device of claim 2, wherein the inserted end is configured to expand and press against an inner surface of the IM canal upon advancement of the tracker pin.

4. The device of claim 1, wherein the tracker pin comprises at least one of a unicortical pin and a bicortical pin.

5. The device of claim 1, wherein the exposed end of the IM canal component is configured to connect to one or more surgical components.

6. The device of claim 5, wherein the one or more surgical components comprise at least one of a replacement joint implant component, a cut guide, and a saw guide.

7. The device of claim 1, wherein the IM canal component further comprises embedded instrumentation configured to provide at least one of position and orientation information.

8. The device of claim 7, wherein the embedded instrumentation comprises at least one of an accelerometer, a gyroscope, a magnetometer, an inertial measurement unit, and a global positioning system device.

9. A system for tracking a tracker array during a surgical procedure, the system comprising:
a surgical navigation system comprising a position tracking system; and
a device for mounting a tracker array onto a patient during the surgical procedure, the device comprising:
an intramedullary (IM) canal component configured to be inserted into an IM canal within a bone, the IM canal component comprising:
an inserted end having a first prong and a second prong forming a slot therebetween, and
an exposed end,
a tracker pin configured to penetrate at least a portion of the bone and engage the inserted end of the IM canal component, wherein the slot is configured to receive at least a portion of the tracker pin, and
a tracker array removably affixed to the tracker pin,
wherein the IM canal component is configured to engage at least a portion of the IM canal of the bone to stabilize the tracker array during the surgical procedure, and
wherein the position tracking system is further configured to track the tracker array removably affixed to the tracker pin during the surgical procedure.

10. The system of claim 9, wherein the first prong comprises at least one aperture configured to receive the tracker pin.

11. The system of claim 10, wherein the inserted end is configured to expand and press against an inner surface of the IM canal upon advancement of the tracker pin.

12. The system of claim 9, wherein the tracker pin comprises at least one of a unicortical pin and a bicortical pin.

13. The system of claim 9, wherein the exposed end of the IM canal component is configured to connect to one or more surgical components.

14. The system of claim 13, wherein the one or more surgical components comprise at least one of a replacement joint implant component, a cut guide, and a saw guide.

15. The system of claim 9, wherein the IM canal component further comprises embedded instrumentation configured to provide at least one of position and orientation information.

16. The system of claim 15, wherein the embedded instrumentation comprises at least one of an accelerometer, a gyroscope, a magnetometer, an inertial measurement unit, and a global positioning system device.

17. A device for mounting a tracker array, the device comprising:
an intramedullary (IM) canal component configured to be inserted into an IM canal within a bone, the IM canal component comprising:
an inserted end having a first prong and a second prong, wherein the first prong comprises at least one aperture, and
an exposed end;
a tracker pin configured to penetrate at least a portion of the bone and engage the inserted end of the IM canal component, wherein the at least one aperture is configured to receive the tracker pin; and
a tracker array removably affixed to the tracker pin,
wherein the IM canal component is configured to engage at least a portion of the IM canal of the bone to stabilize the tracker array during a surgical procedure.

18. The device of claim 17, wherein the inserted end is configured to expand and press against an inner surface of the IM canal upon advancement of the tracker pin.

19. The device of claim 17, wherein the exposed end of the IM canal component is configured to connect to one or more surgical components comprising at least one of a replacement joint implant component, a cut guide, and a saw guide.

20. The device of claim 17, wherein the IM canal component further comprises embedded instrumentation configured to provide at least one of position and orientation information.

* * * * *